United States Patent [19]

Martens et al.

[11] 4,415,738

[45] Nov. 15, 1983

[54] PROCESS FOR THE PRODUCTION THIAZOLINES-(3)

[75] Inventors: Jürgen Martens, Alzenau; Paul Scherberich, Constance; Horst Bethge; Axel Kleemann, both of Hanau, all of Fed. Rep. of Germany

[73] Assignee: Degussa Aktiengesellschaft, Frankfurt, Fed. Rep. of Germany

[21] Appl. No.: 281,858

[22] Filed: Jul. 9, 1981

[30] Foreign Application Priority Data

Jul. 11, 1980 [DE] Fed. Rep. of Germany ....... 3026334

[51] Int. Cl.$^3$ .......................................... C07D 277/08
[52] U.S. Cl. .................................... 548/147; 548/146
[58] Field of Search ................................ 548/146, 147

[56] References Cited

U.S. PATENT DOCUMENTS 3,004,981 10/1961 Asinger .
3,700,682 10/1972 Asinger .
3,931,208 1/1976 Offermanns .
4,153,606 5/1979 Scherberich .

FOREIGN PATENT DOCUMENTS 1063602 8/1959 Fed. Rep. of Germany .
1795299 3/1972 Fed. Rep. of Germany .
2254701 5/1974 Fed. Rep. of Germany .
2645731 4/1978 Fed. Rep. of Germany .

OTHER PUBLICATIONS

Asinger, Angew. Che., Internat. Edit., vol. 6, (1967), pp. 907-919.

Primary Examiner—Robert Gerstl
Attorney, Agent, or Firm—Cushman, Darby & Cushman

[57] ABSTRACT

There are produced thiazoline-(3) compounds which optionally are substituted or unsubstituted in the 2 and-/or 5 positions by reaction of oxo compounds with a metal sulfides, ammonia and oxo compounds which are substituted by halogen in the position adjacent to the oxo group. In this process a mixture of oxo compounds, metal sulfides and ammonia is present and the halogen substituted oxo compound is introduced into the mixture. By using in this manner of mixing, high yields are obtained in a relatively short period of time.

13 Claims, No Drawings

PROCESS FOR THE PRODUCTION THIAZOLINES-(3)

BACKGROUND OF THE INVENTION

The invention is directed to a process for the production of thiazoline-(3) compounds by reaction of an oxo compound with a metal sulfide, ammonia, and an oxo compound which is substituted by halogen in a position adjacent to the oxo group. Thiazoline-(3) compounds serve as oxidation inhibitors for polyolefins. They are also starting materials for the production of sulfur containing amino acids such as cysteine and penicillamine.

It is known to produce 2,5,5-trialkyl substituted thiazoline-(3) compounds by reacting alkylidene vinyl amines with sulfur (Schade German Auslegeschrift No. 1,063,602), or by reaction of an aldehyde branched on the α-carbon atom with sulfur and ammonia (German Offenlegungsschrift No. 1,795,299 and related Asinger U.S. Pat. No. 3,700,683). It is also known that thiazoline-(3) compounds having alkyl substituents in the 2,4 and 5 positions are formed by reacting ketones which have at least one hydrogen atom in the α-position to the oxo group with sulfur and ammonia (Asinger, Angewandte Chemie, International Edition 6 (1967) 907-919, particularly page 908). This process in some cases only results in moderate yields. Besides, according to this process only certain thiazoline-(3) compounds can be recovered. Thiazolines which are not substituted in the 2- or 5- position or in 2-, 4- or 5-positions are not accessible by this process.

Besides, it is known to produce thiazoline-(3) in a given case substituted in the 2,4 and 5 positions by reaction of α-mercaptoaldehydes, α-mercaptoketones or S-acetylated α-mercaptoketones with oxo compounds and ammonia (Asinger, Angewandte Chemie, loc. cit., particularly pages 909 to 910). There are produced thiazoline-(3) compounds, in a given case substituted in the 2,4 and 5 positions from 2,2-dioxodisulfides, oxo compounds, ammonia and hydrogen sulfide (Asinger U.S. Pat. No. 3,004,981) or there are produced 2 and 5 position substituted thiazoline-(3) compounds by such process (Offermanns German OS No. 2,254,701 and related Offermanns U.S. Pat. No. 3,931,208). The disadvantage of this process is that it requires starting materials which are not readily accessible.

Finally, it is known to produce thiazolines-(3) which are substituted or unsubstituted at will in the 2-,4- and or 5-positions by reaction of an oxo compound with a metal sulfide, ammonia and an oxo compound which is substituted on the carbon atom adjacent to the oxo group by halogen, where preferably the oxo compound is present with the metal sulfide and to simultaneously add the ammonia and the oxo compound substituted by halogen (Ger. OS 2645731 and related Scherberich U.S. Pat. No. 4,153,606, e.g. column 4, lines 36-41). In this process there are indeed produced favorable yields but there are needed relatively long reaction times. The entire disclosure of Scherberich U.S. Pat. No. 4,153,606 is hereby incorporated by reference and relied upon.

SUMMARY OF THE INVENTION

There has been found a process for the production of thiazolines-(3) by reacting oxo compounds with metal sulfides, ammonia and oxo compounds which are substituted by halogen on a carbon atom adjacent to the oxo group characterized by having present the oxo compound with the metal sulfide and the ammonia and introducing the halogen substituted oxo compound into this mixture. According to this process the thiazoline-(3) is recovered from relatively easily accessible starting materials. While the known processes are suited in part for the production of thiazolines substituted in specific positions according to the process of the invention there can be produced thiazoline-(3) unsubstituted or substituted in the 2, and/or 5 position with outstanding yields. It is unexpected that by the process of the invention better yields can be obtained in substantially shorter reaction times than in the known processes including those specifically shown in Scherberich U.S. Pat. No. 4,153,606.

According to the invention there are produced thiazoline-(3) compounds of the formula

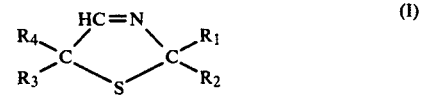

in which $R_1$, $R_2$, $R_3$, and $R_4$ are the same or different and are hydrogen or straight or branched chain alkyl groups with preferably 1 to 18 and especially 1 to 8 carbon atoms or, straight or branched chain alkenyl groups with preferably 2 to 8 and especially 2 to 6 carbon atoms or, where $R_1$ and $R_2$ or $R_3$ and $R_4$ can also be joined to form a closed saturated or unsaturated ring (i.e., including the adjacent carbon atom or carbon atoms of the thiazoline ring) with preferably 3 to 12 and particularly 5 to 8 carbon atoms, or cycloalkyl groups with preferably 3 to 12 and particularly 5 to 8 carbon atoms, or cycloalkenyl groups with preferably 3 to 12 and particularly 5 to 8 carbon atoms, or aryl groups, or alkaryl groups with preferably 1 to 6 and particularly 1 to 2 carbon atoms in each alkyl group, or aralkyl groups with preferably 1 to 6 carbon atoms and particularly 1 to 2 carbon atoms in each alkyl group by reacting (1) an oxo compound of the formula

where $R_1$ and $R_2$ are as defined in formula (I) with an ammonium or metal sulfide, ammonia and an oxo compound of the formula

in which $R_3$ and $R_4$ are as defined in formula (I) and X is chlorine or bromine.

Illustrative of compounds within formula (I) that can be prepared according to the invention are thiazoline-(3); 2,2,5,5-tetramethyl thiazoline-(3); 2,2-pentamethylene-5,5-dimethyl thiazoline-(3); 2,2-diethyl-5,5-dimethyl thiazoline-(3); 2-benzyl-5, 5-dimethyl thiazoline-(3); 2,2-dimethyl-5,5-pentamethylene thiazoline-(3); 2,2-dimethyl-5,5-heptamethylene thiazoline-(3); 2-methyl-2-propyl-5-ethyl-5-butyl thiazoline-(3); 2,2,5,5-tetraethyl thiazoline-(3); 2,2-dihexyl-5,5-dimethyl thiazoline-(3); 2-methyl-2-isopropyl-5,5-dipropyl thiozoline-(3); 2-methyl-2-ethyl-5,5-diisopropyl thiazoline-(3); 2-isopropyl-5,5-dimethyl thiazoline-(3); 2,2,5-trimethyl-5- amyl thiazoline-(3); 2,5,5-trimethyl-2-hexyl thiazoline-(3); 2-allyl-2,5,5-trimethyl thiazoline-(3); 2-butenyl-2-methyl-5,5-diethyl thiazoline-(3); 2,5-dimethyl-2-ethyl-5-butenyl thiazoline-(3); 2-phenethyl-5,5-dimethyl thiazoline-(3); 2,2-dimethyl-5-benzyl-5-ethyl thiazoline-(3); 2,2,5-trimethyl-5-phenethyl thiazoline-(3); 2-phen-propyl-2,2,5-trimethyl thiazoline-(3); 2,2,5,5-di(pentamethylene)-thiazoline-(3); 2,2-pentamethylene-5,5-hexa-methylene thiazoline-(3); 2,2-dimethyl-5,5-octamethylene thiazoline-(3); 2,5,5-trimethyl-2-isopropyl-thiazoline-(3); 2-ethyl-2-phenyl thiazoline-(3); 2,2,5-trimethyl-5-phenyl thiazoline-(3); 2,2-pentamethylene-5-cyclohexyl thiazoline-(3); 2-ethyl-5-t-butyl-thiazoline-(3); 2-methyl-2,5-dibenzyl thiazoline-(3); 2-cyclohexyl-5-ethyl-5-methyl thiazoline-(3); 2-isopropyl-5,5-dimethyl thiazoline-(3); 2,5-dimethyl-2-n-octyl thiazoline-(3); 2-crotyl-5,5-dimethyl thiazoline-(3); 2,2-dimethyl-5-vinyl thiazoline-(3); 2-hexenyl-5,5-dimethyl thiazoline-(3); 2,5,5-trimethyl-2-cyclopentyl thiazoline-(3); 2-p-tolyl thiazoline-(3); 2,5-trimethyl-2-o-tolyl thiazoline-(3); 2,2-dimethyl-5-p-ethylphenyl thiazoline-2-methyl-2-p-hexylphenyl thiazoline-(3).

As oxo compounds of formula (II) there can be used for example formaldehyde; acetaldehyde; propionaldehyde; n-butyraldehyde; cyclopentanealdehyde; cyclohexanealdehyde; cyclooctanealdehyde; cyclooctanealdehyde; cyclododecanaldehyde; valeraldehyde; hexanealdehyde; heptanealdehyde; 2-phenaldehyde; 3-phenyl-propionaldehyde; 4-phenylbutyraldehyde; isobutyraldehyde, sec.-valeraldehyde; acrolein, croton-aldehyde; Δ-6-hexenaldehyde; acetone, methyl ethyl ketone; diethyl ketone; methyl isobutyl ketone; heptanone-4-phenylacetone; pentanone-2; cyclopentanone; cyclohexanone, dibenzyl ketone; cyclooctanone; cyclododecanone; methyl heptyl ketone; dibutyl ketone; di sec.butyl ketone; diisobutyl ketone; divinyl ketone; diallyl ketone; methyl hexen-1-yl ketone; methyl vinyl ketone; ethyl vinyl ketone; methyl allyl ketone; methyl butene-1-yl ketone; diethyl ketone; mesityl oxide; phorone; 2-methyl cyclohexanone-(1); acetophenone; propiophenone; diphenyl ketone; capraldehyde; pelargonaldehyde; lauraldehyde; stearaldehyde; citronellal; benzaldehyde; p-tolualdehyde; di-n-undecyl ketone; di-n-heptadecyl ketone; cinnamaldehyde; methyl n-octadecyl ketone; methyl n-amyl ketone; di-n-propyl ketone; diisopropyl ketone; methyl n-hexyl ketone; methyl n-nonyl ketone; methyl isopropenyl ketone; methyl propenyl ketone; 3-heptenone-(2); crotylidene acetone; phenyl vinyl ketone and phenyl propenyl ketone.

As oxo compounds of formula (III) which have the carbon atom adjacent to the oxo group substituted by halogen there can be used for example 2-bromo-n-butanol-(1); chloroacetaldehyde, 2-chloropropanal-(1); 2-chloro-n-butanal-(1); 2-chloro-2-methylpropanal-(1); 2-bromo-n-pentenal-(1); 2-chloro-2-methylbutanal-(1); 2-chlorobuten-(2)-al-(1); bromoacetaldehyde; 2-chloro-n-nonanal-(1); 2-chloro-n-octadecanal-(1); 2-chloro-n-nonadecanal-(1); 2-chloro-propen-(2)-al-(1); 2-chloro-2-(phenyl) acetaldehyde; 2-chloro-2-(p-tolyl) acetaldehyde; 2-chloro-2-(o-ethylphenyl) acetaldehyde; 2-chloro-2-(benzyl) acetaldehyde; 2-chloro-2-(phenethyl) acetaldehyde.

As metal sulfides there are chiefly employed those which have good solubility in water. For example, these include the hydrogen sulfides of alkaline earth metals and alkali metals. Particularly suited are ammonium hydrogen sulfide and alkaline earth hydrogen sulfides, e.g., calcium hydrogen sulfide and barium hydrogen sulfide and the alkali hydrogen sulfides, especially potassium hydrogen sulfide and sodium hydrogen sulfide.

The ammonia can be added as such or as Diverssche solution ($NH_4NO_3 \cdot 2NH_3$).

The proportions are not critical and can be varied widely. Thus, they can be either stoichiometric, below stoichiometric or over stoichiometric. Generally, however, it is suitable based on the halogen substituted oxo compound (III) to use at least stoichiometric amounts of oxo compound (II), metal (or ammonium hydrogen sulfide and ammonia). Preferably per mole of the halogen substituted oxo compound (III) there are used about 1.5 to 6 moles of oxo compound (II), an amount of metal or ammonium sulfide corresponding to 1 to 2 gram atoms of sulfur and 2 to 3 moles of ammonia.

The materials are brought to reaction either undiluted or diluted by a solvent. As solvents there can be used water or organic liquids or mixtures thereof. As organic solvents there can be used for example lower alkanols such as methanol, ethanol and propanol-(2), saturated aliphatic hydrocarbons such as gasoline fractions, aromatic hydrocarbons such as benzene, toluene and xylene, ethers such as diethyl ether, and halogenated hydrocarbons such as chloroform, carbon tetrachloride, methylene chloride and chlorobenzene. The solvent is in a given case partially or completely introduced with the reacting materials as solutions in the solvents employed.

According to the invention the reaction is carried out by having the oxo compound (II) present with the metal (or ammonium) sulfide and the ammonia and introducing the halogen substituted oxo compound (III) into this mixture. The reaction temperature in a given case is adjusted according to the type of solvent, the type of reacting materials and the proportions. Generally it is suitable to choose temperatures between $-10°$ C. and the boiling point of the reaction mixture. In most cases preferably the temperatures are between about $-10°$ and $+25°$ C.

Unless otherwise indicated all parts and percentages are by weight.

The process can comprise, consist essentially of or consist of the stated steps and materials.

DESCRIPTION OF THE PREFERRED EMBODIMENTS

Example 1

There was present a suspension of 135 grams (2.4 moles) of sodium hydrogen sulfide in a liquid mixture of 450 ml (6.1 moles) of acetone, 93 grams (5.5 moles) of ammonia and 235 grams of water. In the course of 45 minutes there were dropped into this suspension 350 grams of a 45% aqueous solution of chloroacetaldehyde (2.0 moles). The temperature of the reaction mixture during this time and for a further 25 minutes was held at 5° to 10° C. Then the reaction was ended. The 2,2-dimethyl-thiazoline-(3) formed had deposited as an oil. It was separated off and fractionally distilled. The yield was 106 grams, corresponding to 92% based on the chloroacetaldehyde employed. The boiling point of the thiazoline was 88° to 89° C. at 100 mbar.

Example 2

There was present a mixture of 67 grams (1.2 mole) of sodium hydrogen sulfide, 220 grams (3.0 moles) of butanone-(2), 47 grams (2.7 moles) of ammonia and 100 ml of water. In the course of 60 minutes there were dropped into this mixture 175 grams of a 45% aqueous solution of chloroacetaldehyde (1.0 mole). The temperature was held at 10° to 20° C. during this time and for a further 15 minutes. The yield of 2-methyl-2-ethyl-thiazoline-(3) was 124 grams, corresponding to 89% based on the chloroacetaldehyde employed. The boiling point of the thiazoline was 52° to 55° C. at 16 mbar.

Example 3

There were present 517 grams (6.0 moles) of diethyl ketone, a solution of 160 grams (2.2 moles) of potassium hydrogen sulfide in 200 ml of water and 94 grams (5.5 moles) of ammonia. There were added in the course of 60 minutes 350 grams of a 45% aqueous solution of chloroacetaldehyde (2.2 moles). The temperature was held during this time and for a further 15 minutes at 0° to 10° C. The yield of 2,2-diethyl-thiazoline-(3) was 110 grams, corresponding to 78% based on the chloroacetaldehyde employed. The boiling point of the thiazoline was 77° to 80° C. at 16 mbar.

Example 4

There were present 245 grams (2.5 moles) of cyclohexanone, a solution of 80 grams (1.1 moles) of potassium hydrogen sulfide in 100 ml of water and 47 grams (2.7 moles) of ammonia. There were added in the course of 75 minutes 175 grams of a 45% aqueous solution of chloroacetaldehyde. The reaction mixture was held under reflux at the boiling temperature during this time. The yield of 2,2-pentamethylene thiazoline-(3) was 126 grams, corresponding to 80% based on the chloroacetaldehyde employed. The boiling point of the thiazoline was 100° to 105° C. at 16 mbar.

What is claimed is:

1. In a process for preparing a thiazoline-(3) compound of the formula

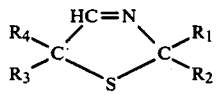
(I)

in which $R_1$, $R_2$, $R_3$, and $R_4$ individually are hydrogen, alkyl, alkenyl, cycloalkyl, cycloalkenyl, aryl, alkaryl, or aralkyl or $R_1$ and $R_2$ are joined together or $R_3$ and $R_4$ are joined together and form which the carbon atom or atoms of the thiazoline ring to which they are connected a ring by reacting (1) an oxo compound of the formula

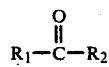
(II)

(2) a metal or ammonium hydrogen sulfide, (3) ammonia and (4) an oxo compound having a halogen atom on the carbon atom adjacent to the carbonyl group and having the formula

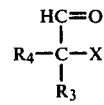
(III)

where X is chlorine or bromine, the improvement comprising having reactants (1), (2), and (3) present as a mixture and adding reactant (4) to said mixture.

2. The process of claim 1 wherein $R_1$, $R_2$, $R_3$, and $R_4$ individually are hydrogen, alkyl 1 to 18 carbon atoms, cycloalkyl of 3 to 12 carbon atoms, cycloalkenyl of 3 to 12 carbon atoms, phenyl, alkylphenyl with 1 to 6 carbon atoms in the alkyl group or phenylalkyl with 1 to 6 carbon atoms in the alkyl group or $R_1$ and $R_2$ together or $R_3$ and $R_4$ together are alkylene of 3 to 12 carbon atoms.

3. The process of claim 2 wherein (2) is an alkali metal, an alkaline earth metal or ammonium hydrogen sulfide.

4. The process of claim 3 wherein (2) is sodium hydrogen sulfide, potassium hydrogen sulfide or ammonium hydrogen sulfide.

5. The process of claim 2 wherein $R_1$, $R_2$, $R_3$, and $R_4$ individually are hydrogen, alkyl of 1 to 8 carbon atoms, alkenyl of 2 to 6 carbon atoms, cycloalkyl with 5 to 8 carbon atoms, cycloalkenyl with 5 to 8 carbon atoms, phenyl, alkylphenyl with 1 to 2 carbon atoms in the alkyl group, phenalkyl with 1 to 2 carbon atoms in the alkyl group or $R_1$ and $R_2$ together or $R_3$ and $R_4$ together are alkylene of 5 to 8 carbon atoms.

6. The process of claim 2 wherein $R_1$, $R_2$, $R_3$, and $R_4$ individually are hydrogen, alkyl of 1 to 3 carbon atoms, alkenyl of 2 to 4 carbon atoms, cycloalkyl of 5 to 6 carbon atoms or phenyl and $R_1$ and $R_2$ together or $R_3$ and $R_4$ together are alkylene of 5 to 8 carbon atoms.

7. The process of claim 6 wherein $R_1$ individually is hydrogen or alkyl of 1 to 3 carbon atoms, $R_2$ individually is hydrogen or alkyl of 1 to 2 carbon atoms, $R_3$ is hydrogen, methyl or phenyl, $R_4$ is hydrogen or methyl or $R_1$ and $R_2$ together are pentamethylene.

8. A process according to claim 2 wherein reactant (1) is a ketone.

9. A process according to claim 2 wherein $R_3$ is other than hydrogen.

10. A process according to claim 4 wherein reactant (1) is acetone, butanone-(2), diethyl ketone or cyclohexanone and reactant (4) is chloroacetaldehyde.

11. A process according to claim 10 wherein the reaction is carried out in the presence of water as a solvent for the chloroacetaldehyde.

12. A process according to claim 1 carried out in the presence of water as a solvent.

13. A process according to claim 12 wherein per mole of halogen substituted oxo (4) there are employed 1.5 to 6 moles of oxo reactant (1), an amount of metal or ammonium sulfide (2) to 1 to 2 gram atoms of sulfur and 2 to 3 moles of ammonia.

* * * * *